ical-rotatio

(12) United States Patent
Greene et al.

(10) Patent No.: US 9,265,739 B2
(45) Date of Patent: Feb. 23, 2016

(54) METHODS AND USE OF COMPOUNDS THAT BIND TO HER2/NEU RECEPTOR COMPLEX

(75) Inventors: Mark I. Greene, Penn Valley, PA (US); Ramachandran Murali, Beverly Hills, CA (US); Hongtao Zhang, Paoli, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 476 days.

(21) Appl. No.: 13/700,915

(22) PCT Filed: May 26, 2011

(86) PCT No.: PCT/US2011/038044
§ 371 (c)(1),
(2), (4) Date: Feb. 7, 2013

(87) PCT Pub. No.: WO2011/153050
PCT Pub. Date: Dec. 8, 2011

(65) Prior Publication Data
US 2013/0137774 A1 May 30, 2013

Related U.S. Application Data

(60) Provisional application No. 61/350,700, filed on Jun. 2, 2010.

(51) Int. Cl.
*A61K 31/165* (2006.01)
*A61K 51/04* (2006.01)
*G01N 33/574* (2006.01)
*A61K 45/06* (2006.01)

(52) U.S. Cl.
CPC ............... *A61K 31/165* (2013.01); *A61K 45/06* (2013.01); *A61K 51/04* (2013.01); *G01N 33/574* (2013.01); *G01N 2333/71* (2013.01)

(58) Field of Classification Search
CPC ............................. A61K 31/165; A61K 45/06
See application file for complete search history.

(56) References Cited

U.S. PATENT DOCUMENTS

| | | | |
|---|---|---|---|
| 5,217,999 A | 6/1993 | Levitzki et al. | |
| 5,302,606 A | 4/1994 | Spada et al. | |
| 5,330,992 A | 7/1994 | Eissenstat et al. | |
| 5,596,878 A | 1/1997 | Hanson et al. | |
| 5,710,173 A | 1/1998 | Tang et al. | |
| 6,225,346 B1 | 5/2001 | Tang et al. | |
| 6,596,878 B2 | 7/2003 | Chen et al. | |
| 6,716,859 B2 | 4/2004 | Drewe et al. | |
| 6,716,863 B2 | 4/2004 | Tasaka et al. | |
| 6,984,653 B2 | 1/2006 | Tasaka et al. | |
| 7,300,935 B2 | 11/2007 | Cho et al. | |
| 2005/0148607 A1 | 7/2005 | Suzuki et al. | |
| 2006/0009493 A1 | 1/2006 | Koenig et al. | |
| 2006/0025430 A1 | 2/2006 | Mishani et al. | |
| 2008/0214584 A1 | 9/2008 | Ohta et al. | |

FOREIGN PATENT DOCUMENTS

| | | |
|---|---|---|
| WO | WO 91/15495 A1 | 10/1991 |
| WO | WO 92/20642 A1 | 11/1992 |
| WO | WO 92/21660 A1 | 12/1992 |
| WO | WO 94/03427 A1 | 2/1994 |
| WO | WO 94/14808 A1 | 7/1994 |
| WO | WO 96/00226 A1 | 1/1996 |
| WO | WO 97/13771 A1 | 4/1997 |
| WO | WO 98/02437 A1 | 1/1998 |
| WO | WO 01/01921 A1 | 1/2001 |
| WO | WO 01/77107 A1 | 10/2001 |
| WO | WO 01/98277 A2 | 12/2001 |
| WO | WO 01/98299 A1 | 12/2001 |
| WO | WO 02/02552 A1 | 1/2002 |
| WO | WO 03/000688 A1 | 1/2003 |
| WO | WO 03/049740 A1 | 6/2003 |
| WO | WO 03/050108 A1 | 6/2003 |
| WO | WO 03/053446 A1 | 7/2003 |
| WO | WO 2004/031232 A1 | 4/2004 |

OTHER PUBLICATIONS

Adams, et al., "Humanization of a recombinant monoclonal antibody to produce a therapeutic HER dimerization inhibitor, pertuzumab", Cancer Immunol. Immunother. Jun. 2006 [Epub Sep. 3, 2005], 55(6), 717-27.

Berge et al., "Pharmaceutical Salts", J. Pharm. Sci., 1977, 66, pp. 1-19.

Drebin et al., "Down-modulation of an oncogene protein product and reversion of the transformed phenotype by monoclonal antibodies", Cell, Jul. 1985, 41(13), 695-706.

Fukazawa et al. "A microplate assay for quantitation of anchorage-independent growth of transformed cells", Anal. Biochem., Jun. 1995, 10, 83-90.

Signoretti, S. et al., "Her-2-neu expression and progression toward androgen independence in human prostate cancer", Journal of the National Cancer Institute, Dec. 2000, 92(23), 918-1925.

Masuda et al., "AHNP-streptavidin: a tetrameric bacterially produced antibody surrogate fusion protein against p185her2/neu," Oncogene, Dec. 14, 2006, 25(59), 7740-7746.

Olayioye MA (2001). "Update on Her-2 as a target for cancer therapy: intracellular signaling pathways of ErbB2/Her-2 and family members," Breast Cancer Res. 2001 [Epub Oct. 4, 2001] 3(6):385-389.

Slamon, D. J., et al., "Human breast cancer: correlation of relapse and survival with amplification of the HER-2/neu oncogene", Science, Jan. 1987, 235, 177-182.

(Continued)

*Primary Examiner* — Samira Jean-Louis
(74) *Attorney, Agent, or Firm* — Baker & Hostetler, LLP

(57) ABSTRACT

This application describes pharmaceutical compositions, commercial packages, and methods for inhibiting cell proliferative disorders, especially those disorders, including Her2 related cancers, characterized by overactivity and/or inappropriate activity of a receptor tyrosine kinase, and methods for imaging an HER-2 expressing tumor.

17 Claims, 4 Drawing Sheets

(56) References Cited

OTHER PUBLICATIONS

Ye et al., "Augmentation of a humanized anti-HER2 mAb 4D5 induced growth inhibition by a human-mouse chimeric anti-EGF receptor mAb C225", Oncogene, Jan. 21, 1999, 18(3), 731-738.

Baselga; "Treatment of HER2-overexpressing breast cancer"; Annals of Oncology; vol. 21 Issue 7; 2010; p. vii36-40.

Ahmad et al.; "HER2 overcomes PTEN (loss)-induced senescence to cause aggressive prostate cancer"; Proc. Nat'l Acad. Science; vol. 108; 2011; p. 16392-16397.

Shigematsu et al.; "Somatic Mutations of the HER2 Kinase Domain in Lung Adenocarcinomas"; Cancer Research; vol. 65; Mar. 2005; p. 1642-1646.

Komoto et al.; "HER2 overexpression correlates with survival after curative resection of pancreatic cancer"; Cancer Science; vol. 100 Issue 7; Jul. 2009; p. 1243-1247.

Meden et al.; "Overexpression of the oncogene c-erbB-2 (HER2/neu) in ovarian cancer: a new prognostic factor"; European Journal of Obstetrics & Gynecology; vol. 71 Issue 2; Feb. 1997; p. 173-179.

Gravalos et al.; "HER2 in gastric cancer: a new prognostic factor and a novel therapeutic target"; Annals of Oncology; vol. 19 Issue 9; Sep. 2008; p. 1523-1529.

METHODS AND USE OF COMPOUNDS THAT BIND TO HER2/NEU RECEPTOR COMPLEX

CROSS-REFERENCE TO RELATED APPLICATIONS

This application is the National Stage of International Application No. PCT/US2011/038044, filed May 26, 2011, which claims the benefit of U.S. Provisional Application No. 61/350,700 filed Jun. 2, 2010, the disclosures of which are incorporated herein by reference in their entireties.

TECHNICAL FIELD

This invention is in the fields of cancer diagnosis and therapy. More particularly it concerns compounds which are useful agents for inhibiting cell proliferative disorders, especially those disorders, including Her2 related cancers, characterized by over activity and/or inappropriate activity of a receptor tyrosine kinase and methods for treating these disorders. It also describes methods for measuring and monitoring growth of tumors.

BACKGROUND

Cancer affects approximately 10 million people globally and it is expected to increase to 15 million by 2020. Worldwide approximately 23 million people are living with cancer and about 5.2 million people die. Breast and lung cancer account for 25% of cancer incidences.

Expression of Human Epidermal growth factor receptor 2 (or "Her2") in breast cancer, prostate cancer, lung cancer, gastric cancer and the like has been reported and Her2 is considered to be involved in the growth of these cancers. For example, Slamon et al., Science 235, 177 (1987) demonstrated that about 30% of primary human breast carcinoma tumors contained an amplified Her2 gene. More recently, it has been reported that about 25% of primary prostate cancer is Her2 expression positive, and the percentage increases along with the progression of the cancer (Journal of the National Cancer Institute, Vol. 92, No. 23, pp. 1918-1925 (2000)). Similarly, 4-27% of lung cancer cases are reported to overexpress Her2/neu (ErbB2). Overexpression of HER2/neu and other erbB receptors is associated with increased disease recurrence and leads to a poor prognosis in such cancers.

Many other diseased states are also characterized by the uncontrolled reproduction of cells. These diseased states involve a variety of cell types and, in addition to leukemia and cancer, include psoriasis, atherosclerosis and restenosis injuries. The inhibition of tyrosine kinase is believed to have utility in the control of uncontrolled cellular reproduction, i.e., cellular proliferative disorders Her2 is also known as neu, ErbB-2, or ERBB2. Her2/neu (ErbB2), a member of the type I transmembrane receptor tyrosine kinase family, regulates cell differentiation and growth during embryogenesis and breast development. This oncogene was first obtained from rat neuroglioblastoma induced by a chemical carcinogenic substance was found to encode a protein belonging to the EGF receptor family, and the relationship with which was suggested. Thereafter, an neu human homologue was isolated and named as ERBB2 or Her2 based on the similarity to an EGF receptor, ERBB (avian erythroblastosis oncogene B). The oncogene later found to code for EGFR (Epidermal Growth Factor Receptor). Gene cloning subsequently determined that neu, Her2, and erbB2 are species variants of one another. (Slamon, D. J., et al., Science, 235:177 182, 1987).

ErbB receptors or epidermal growth factor receptors (EGFR) play an important role in a variety of signal transduction pathways that promote cell differentiation, growth, proliferation, and migration. Interaction between Erb receptors allows ErbB2/Her2 to participate in effective signaling. In particular, EGFR and Her2 have been implicated in the development of human cancer, hence Her2 represents an attractive therapeutic target against Her2 positive cancers.

Her2 is a cell membrane surface bound receptor tyrosine kinase, normally involved in the signal transduction pathways leading to cell proliferation, differentiation, and migration. Co-expression of Her2/neu and other members of erbB in normal cells promotes formation of dimer complexes, which cause malignant cell transformation. Olayioye M A (2001). "Update on Her-2 as a target for cancer therapy: intracellular signaling pathways of ErbB2/Her-2 and family members," Breast Cancer Res. 3(6): 385-389.

Her2 hardly expresses in normal tissues. Therefore, an Her2 selective therapeutic drug would be cancer selective, with the reduced toxicity or extremely few side effects. This means that an extreme safe and highly versatile treatment method could be provided, which is strikingly different from conventional cancer chemotherapeutic agents.

Currently, the only drugs that can disable both Her2 and EGFr function (Trastuzumab or Herceptin, Pertuzumab, and similar humanized monoclonal antibodies) are targeted to receptor tyrosine kinase in the cytoplasmic domains. Small molecule tyrosine kinase inhibitors such as the quinazolinamine, Lapatinib (N-[3-chloro-4-[(3-fluorophenyl)methoxy]phenyl]-6-[5-[(2-methylsulfonylethylamino)methyl]-2-furyl]quinazolin-4-amine), which compete for ATP binding sites on the tyrosine kinase domain of receptors are also being used to treat Her2 positive tumors.

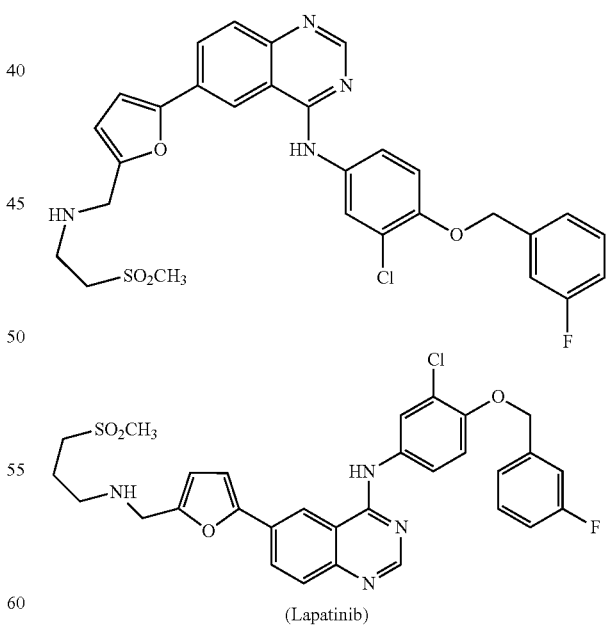

(Lapatinib)

Attempts have also been made to identify other small molecules which act as tyrosine kinase inhibitors, and other compounds inhibiting a receptor-type tyrosine kinase (including Her2/EGFR kinase) include fused heterocyclic compounds such as compounds generally depicted as

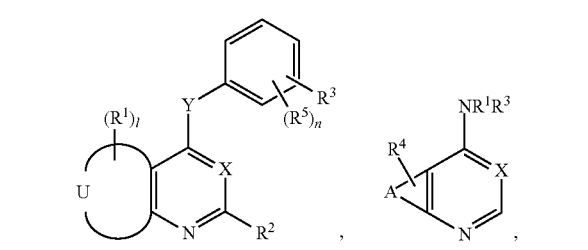
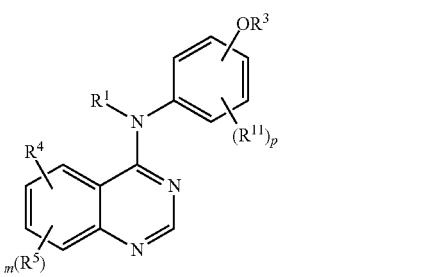
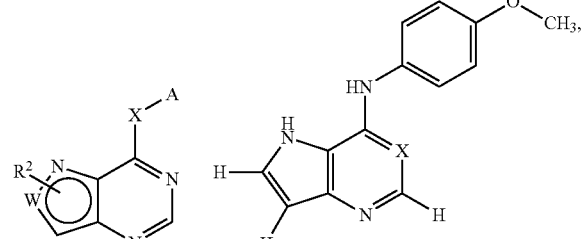
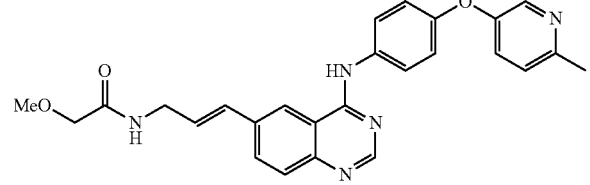
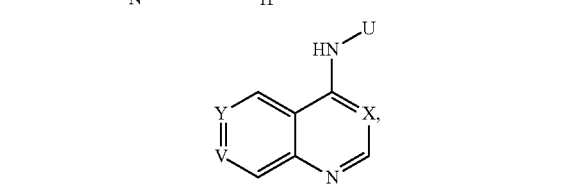
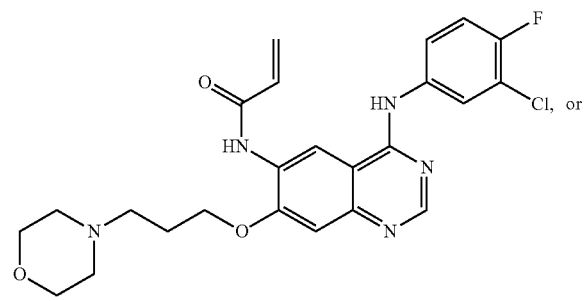
(see, for example, WO02/02552, WO01/98277, WO03/049740 and WO03/050108, U.S. Pat. No. 6,596,878), thienopyrimidine derivatives such as compounds generally depicted as
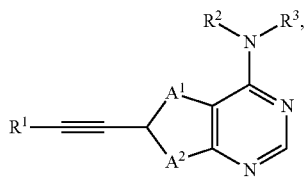
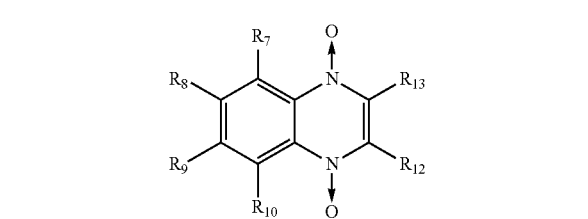
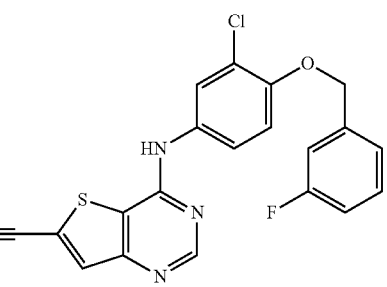
(see, for example, WO97/13771, WO98/02437, WO00/44728, U.S. Pat. No. 6,596,878, US 2005/0148607, and US 2008/0214584), quinazoline derivatives such as compounds generally depicted as
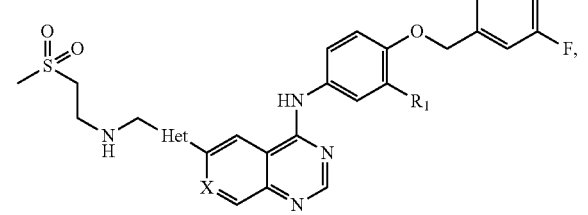
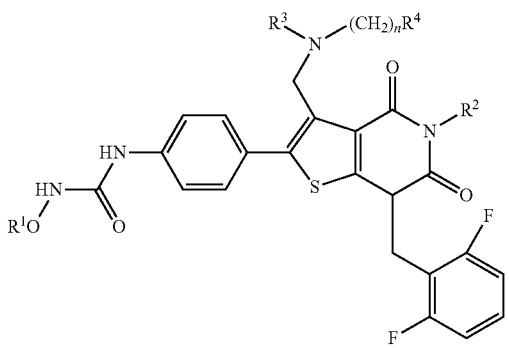
or
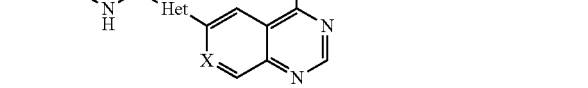

(see, for example, WO03/053446, U.S. Pat. No. 7,300,935), thienyl derivatives such as compounds generally depicted as

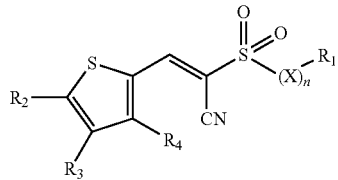

(see for example, U.S. Pat. No. 5,710,173), aromatic azole derivatives such as compounds generally depicted as

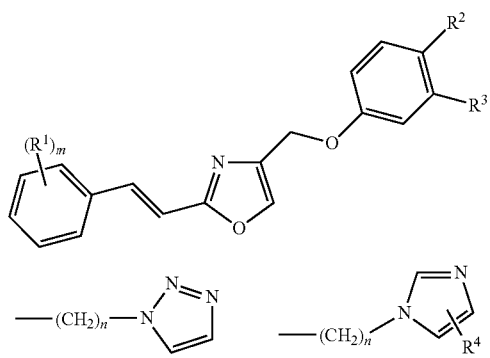

(see, for example, WO01/77107, WO03/031442, U.S. Pat. Nos. 6,716,863 and 6,984,653), and the like are known.

Further, bis monocyclic, bicyclic or heterocyclic aryl compounds such as compounds generally depicted as

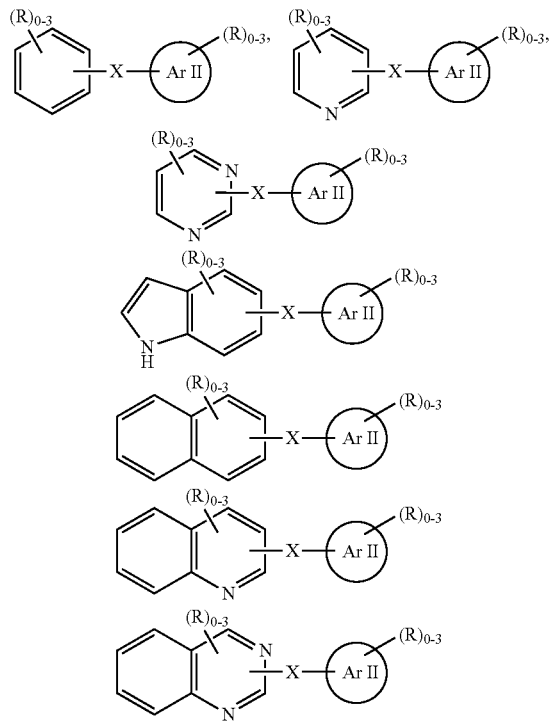

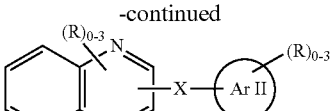
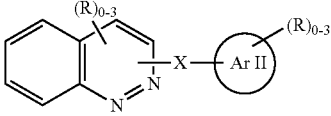
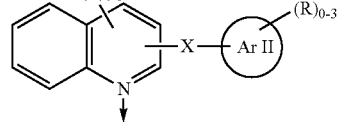
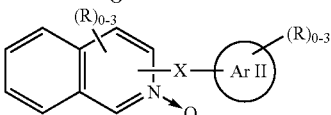
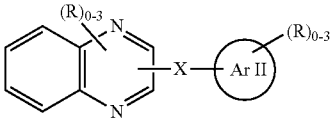

(see, for example, WO 92/20642), vinylene-azaindole derivatives such as compounds generally depicted as

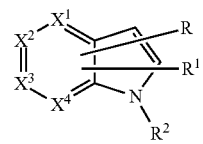

(see, for example, WO94/14808), azaindoles such as compounds generally depicted as

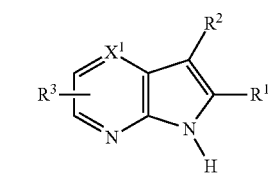

(see, for example, WO03/000688 and WO96/000226) and 1-cyloproppyl-4-pyridyl-quinolones such as compounds generally depicted as

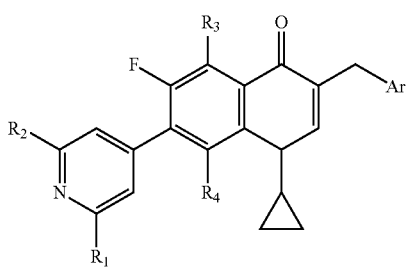

(see, for example, U.S. Pat. No. 5,330,992) have been described generally as tyrosine kinase inhibitors. Styryl compounds such as compounds generally depicted as

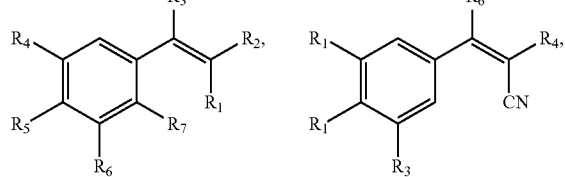

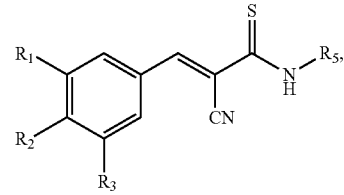

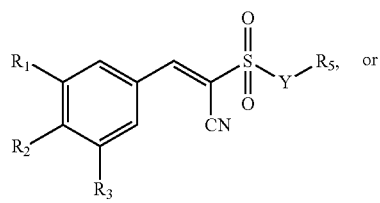

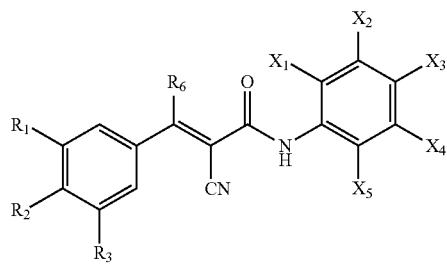

(see, for example, U.S. Pat. Nos. 5,217,999, 5,596,878), styryl-substituted pyridyl compounds such as compounds generally depicted as

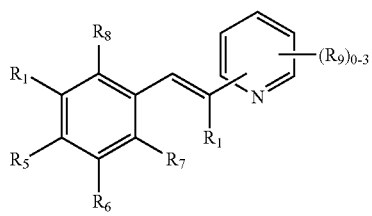

(see, for example, U.S. Pat. No. 5,302,606), tyrphostin-like compounds such as compounds generally depicted as

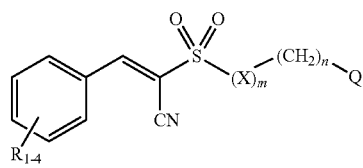

(see, for example, U.S. Pat. No. 6,225,346), seleoindoles and selenides such as compounds generally depicted as

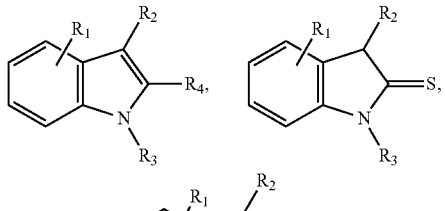

(see, for example, WO94/03427), 1H-pyrrolo[2,3-b]pyridines such as compounds generally depicted as

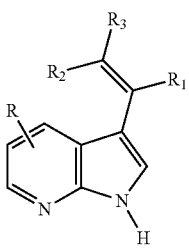

(see, for example, WO01/098299), tricyclic polyhydroxylic compounds such as compounds generally depicted as

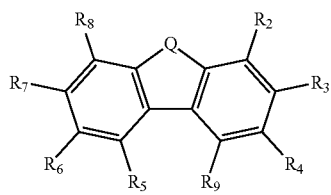

(see, for example, WO92/21660), 2-pyrazolin-5-ones such as compounds generally depicted as

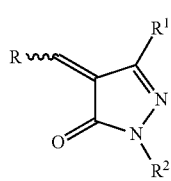

(see, for example, WO 01/01921), and benzylphosphonic acid compounds such as compounds generally depicted as

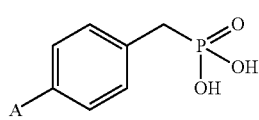

(see, for example, WO91/15495) have been described as compounds for use as tyrosine kinase inhibitors for use in the treatment of cancer.

While drugs targeted to the receptor-type tyrosine kinase enzyme have shown promise in treating some cancers, the concern remains that chronic use of such agents that depend on tyrosine kinase domain receptors may lead to acquired resistance in patients. Indeed, such resistance may be seen within 12 months of the treatment with such agents. It is believed that these reflect the fact that kinase domains can alter their structure and become resistant over regular use. Beyond this, the structure of kinase domain is ubiquitous and highly conserved and long use of kinase inhibitors can inhibit other kinases involved in the development of cells/organs. Thus, these kinase domain targeted drugs may be unsuitable for small children with cancers.

SUMMARY

The present invention relates to use of small molecule compounds to modulate or inhibit the activity of a receptor tyrosine kinase.

In some embodiments, the invention teaches a method of inhibiting a cell proliferative disorder characterized by over-activity and/or inappropriate activity of a receptor, especially an Her2 receptor, comprising administering to a patient in need of such treatment a pharmaceutically effective amount of a compound of Formula (A), or a pharmaceutically acceptable salt or prodrug thereof:

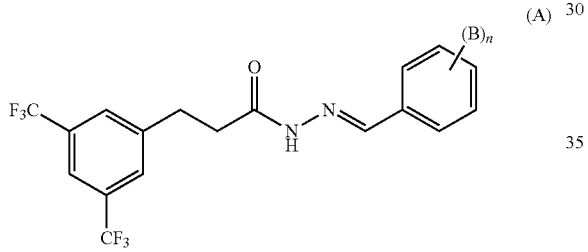

(A)

where n is 1-5 and B is independently alkyl, hydroxy, halo, perfluoromethyl, carboxylic acid, ester, amide, substituted alkoxy, substituted thiol, substituted acyl, nitrile, or substituted amino group.

In other embodiments, the invention teaches a method of inhibiting a cell proliferative disorder characterized by over-activity and/or inappropriate activity of a protein tyrosine kinase portion of a receptor, especially an Her2 receptor, comprising administering to a patient in need of such treatment a pharmaceutically effective amount of a compound of Formula (I), or a pharmaceutically acceptable salt or prodrug thereof:

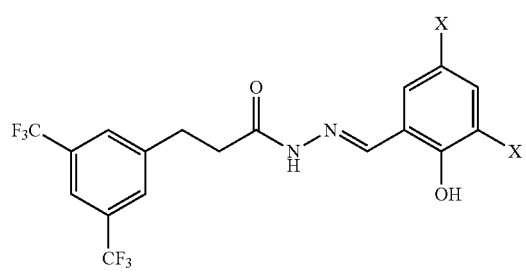

(I)

or its tautomer

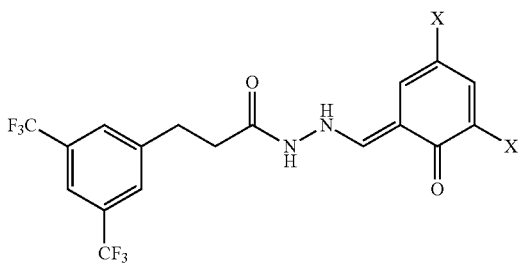

wherein X is independently at each occurrence a hydrogen, halo, hydroxy, carboxylic acid, ester, amide, substituted alkoxy, substituted thiol, substituted acyl, nitrile, or substituted amino group.

In still other embodiments, the compound is of Formula (I) wherein X is halo, preferably chloro or iodo, most preferably chloro.

In still other embodiments, the compound of Formula (I) is

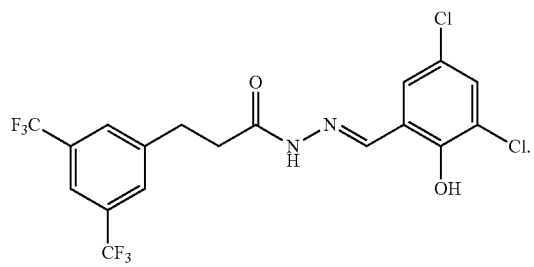 [SMILES: O=C(CCc1cc(C(F)(F)F)cc(C(F)(F)F)c1)N/N=C/c1cc(Cl)cc(Cl)c1O]

In further embodiments, the invention discloses a method of treating a patient having a disease characterized by over-activity and/or inappropriate activity of a protein tyrosine kinase portion of a receptor, especially an Her2 receptor, comprising the step of administering to said patient a pharmaceutically effective amount of a compound having the Formula (I), of any of the previously cited chemical embodiments.

In still further embodiments, the invention teaches the use of a compound of any of the preceding chemical embodiments of Formula (I) for the preparation of a medicament for the inhibition of a cell proliferative disorders characterized by over-activity and/or inappropriate activity of a protein tyrosine kinase portion of a receptor, especially an Her2 receptor, and in still other embodiments, the invention discloses a pharmaceutical composition comprising a compound of Formula (I) in an amount effective to inhibit a cell proliferative disorder characterized by over-activity and/or inappropriate activity of a protein tyrosine kinase portion of a receptor, especially an Her2 receptor. Each pharmaceutical compound embodiment may be part of a commercial package, further comprising at least one anti-cancer agent and written instructions as to the use of the medicament.

In each of these embodiments, the receptor can include an erbB receptor, preferably an epidermal growth factor receptor (EGFR), or a platelet-derived growth factor receptor, and/or the receptor is Her2, Her3, or Her4, such that the aim of the method or composition is to inhibit the overexpression or activation of Her2, Her3, or Her4 and/or EGFR, thereby inhibiting associated diseases such as cancer, angiogenesis associated with the growth of cancer or sarcoma, angiogenesis associated with cancer metastasis, angiogenesis associated with diabetic retinopathy, arteriosclerosis, restenosis, or psoriasis. Exemplary cancers include breast, prostate, lung, pancreatic, ovarian, or stomach cancers.

In other embodiments, the patient being treated or to whom the composition is to be applied is a human.

This invention can be applied to treat cell proliferative disorders, such as cancers characterized by the over-activity or inappropriate activity of Her2/neu, when used alone or in combination with chemotherapy (e.g., cytotoxic chemotherapy or radiation or both) to halt resistance to currently available drugs. The invention may also be applied in combination with administering a pharmaceutically effective amount of an anti-cancer agent or performing a non-drug therapy or both on the patient.

The invention provides a novel class of Her2 and EGFR inhibitors that may halt the resistance to current tyrosine kinase inhibitors hence increase treatment efficacy, and as such provide an alternative to the use of current tyrosine kinase inhibitors. The described compounds inhibit the overexpression of Her2, EGFR, Her3, and/or Her4 complexes. The discovered molecules, which are attainable for oral administration, can be used alone or in combination with cytotoxic drugs, hormonal agent, radiation, or other Her2 inhibitors to treat breast, lung, prostate, and other Her2-associated cancers. In addition, the discovered compounds exhibit great specificity against Her2/EGFR activity by selectively binding to only Her2 or Her2 associated dimers (for example Her2 homodimer, Her2-EGFR heterodimer, Her2-Her3 heterodimer and her2-her4 heterodimer). This might cause less severe side effects in comparison to the conventional tyrosine kinase inhibitors.

The small molecules describe by this invention can also be "tagged" with radio-isotopes for molecular imaging of tumor marker Her2 in vivo. Radio-labeled compounds are required for Positron Emission Tomography (PET) and Single Photon Emission Computed Tomography (SPECT). In vivo monitoring of the Her2 expressing tumor is useful in monitoring the disease progression and assessing the treatment efficacy. Accordingly, the invention discloses a method of imaging an Her2 expressing tumor comprising administering a marker to a patient having said Her2 expressing tumor, said marker comprising a compound of Formula (I) containing an imaging enhancing agent.

Groups of compounds able to inhibit Her2/neu receptors are described herein.

DETAILED DESCRIPTION OF ILLUSTRATIVE EMBODIMENTS

Figure 1:
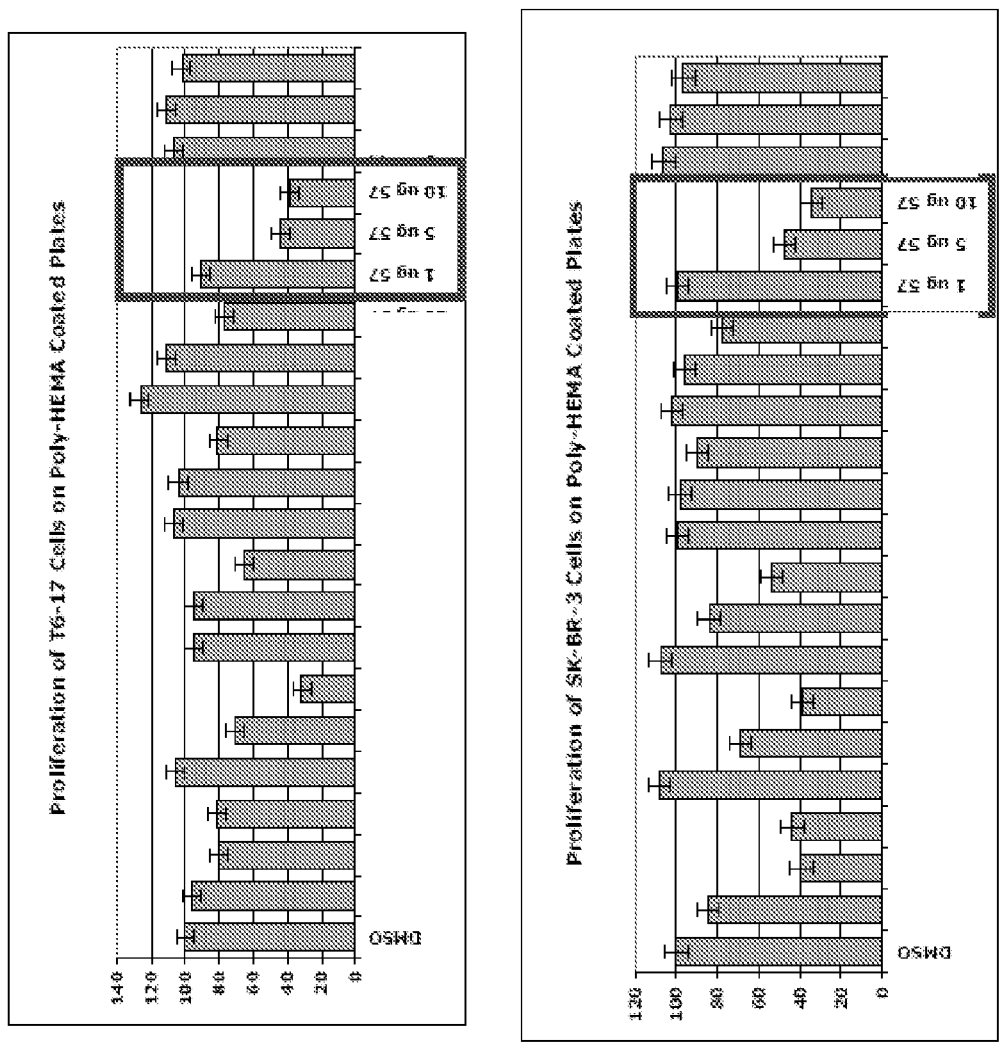
FIG. 1 shows the results of screening, according to the procedure in Example 1, to show the effect of EGFR and Her2 inhibitors on T6-17 and SK-BR-3 cell proliferation. Data for compound #S22_57 are highlighted (as "057"), showing reduced cellular growth in culture (p<0.05).

The present invention may be understood more readily by reference to the following detailed description taken in connection with the accompanying Figures and Examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the compounds and to the resulting pharmaceutical compositions and methods of manufacture and use.

The present invention relates to use of small molecule compounds to modulate or inhibit the activity of a receptor tyrosine kinase.

In various embodiments, the invention relates to a method of inhibiting a cell proliferative disorder characterized by over-activity and/or inappropriate activity of a protein tyrosine kinase portion of a receptor, especially an Her2 receptor, comprising administering to a patient in need of such treatment a pharmaceutically effective amount of a compound of Formula (A), or a pharmaceutically acceptable salt or prodrug thereof:

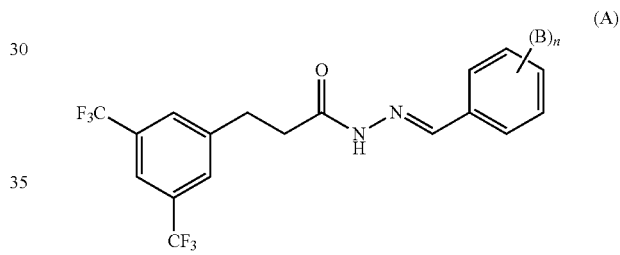

where n is 1-5 and B is independently alkyl, hydroxy, halo, perfluoromethyl, carboxylic acid, ester, amide, substituted alkoxy, substituted thiol, substituted acyl, nitrile, or substituted amino group.

In certain embodiments, the invention teaches a method of inhibiting a cell proliferative disorder characterized by over-activity and/or inappropriate activity of a receptor, including an erbB receptor, preferably an epidermal growth factor receptor (EGFR), or a platelet-derived growth factor receptor, and/or the receptor is Her2, Her3, or Her4, preferably and Her2 receptor, comprising administering to a patient in need of such treatment a pharmaceutically effective amount of a compound of Formula (I), or a pharmaceutically acceptable salt or prodrug thereof:

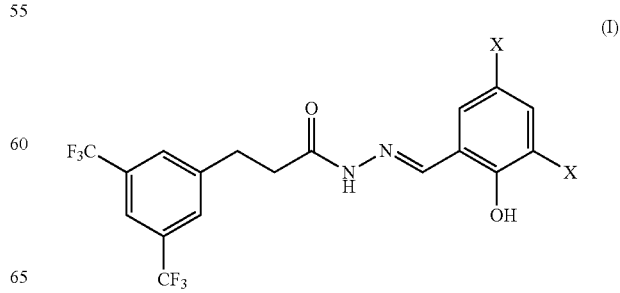

or its tautomer

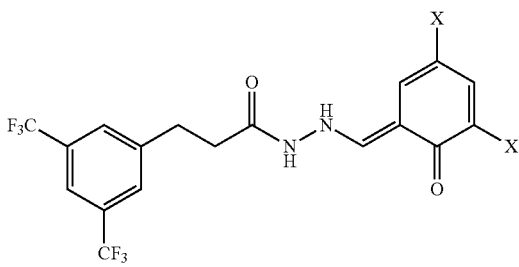

wherein X is independently at each occurrence a hydrogen, halo, hydroxy, carboxylic acid, ester, amide, substituted alkoxy, substituted thiol, substituted acyl, nitrile, or substituted amino group.

It should be appreciated that additional functionalization of the compound can be achieved at both the alcohol-oxygen or amino-nitrogen positions. The skilled artisan will appreciate that such substitutions may include alkylation or acylation and that the preferred site of this functionalization depends on the nature of the functionalizing agent (e.g., selective protecting groups).

In other embodiments, the X moiety of the compound of Formula (I) is halo, preferably independently chloro or iodo, or more preferably both chloro:

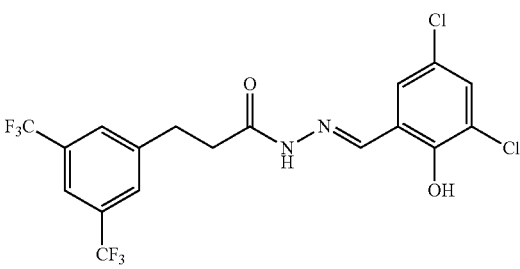

which can also be represented as:

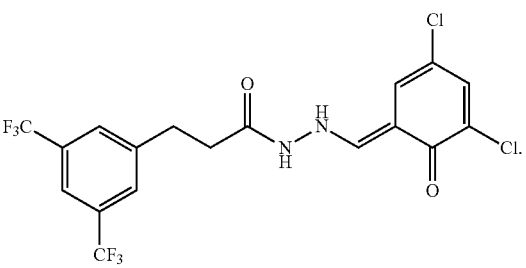

This latter compound is described within the Experimental section below as SS22_57, and is commercially available from Maybridge Chemicals, UK, Catalog #CD04155SC.

The skilled artisan will recognize that the substitutions of the aromatic halides of SS22_57 with groups including hydrogen, halo, hydroxy, carboxylic acids, esters, amides, substituted alkoxy, substituted thiols, substituted acyl, nitriles, and substituted amino groups. The latter allow for a wide range of X substituents from the SS22_57 structure, all of which fall within the scope of this invention. For means to affect the specific transformations described herein, see, e.g., J. March, Advanced Organic Chemistry, 2d ed., McGraw Hill (1977), which is incorporated by reference in its entirety.

The sequences set forth herein are illustrative only, and are not intended to limit the scope of the invention. Those skilled in the art will appreciate that modifications to the described synthetic schemes can be performed without detracting from the spirit of the invention.

The various substituents can be selected in view of factors such as, for example, absorption, activity, affinity, distribution, excretion, metabolism, pharmacokinetic, solubility, toxicological and other properties conducive to their use as pharmaceuticals.

In further embodiments, the invention discloses a method of treating a patient having a disease characterized by over-activity and/or inappropriate activity of a receptor, including an erbB receptor, preferably an EGFR or a platelet-derived growth factor receptor, and/or the receptor is Her2, Her3, or Her4, preferably and Her2 receptor, comprising the step of administering to said patient a pharmaceutically effective amount of a compound having the Formula (I), of any of the previously cited chemical embodiments.

In still further embodiments, the invention teaches the use of a compound of any of the preceding chemical embodiments of Formula (I) for the preparation of a medicament for the inhibition of a cell proliferative disorders characterized by over-activity and/or inappropriate activity of a receptor, including an erbB receptor, preferably an EGFR growth factor, or a platelet-derived growth factor receptor, and/or the receptor is Her2, Her3, or Her4, preferably and Her2 receptor, and in still other embodiments, the invention discloses a pharmaceutical composition comprising a compound of Formula (I) in an amount effective to inhibit a cell proliferative disorder characterized by over-activity and/or inappropriate activity of a protein tyrosine kinase portion of a receptor, especially an Her2 receptor.

Each pharmaceutical compound embodiment may also be part of a commercial package, further comprising at least one anti-cancer agent and written instructions as to the use of the medicament. Such instructions may include, for example, written matter stating that the pharmaceutical composition can or should be used for the prophylaxis and/or treatment of a disease caused by overexpression or activation of Her2 and/or EGFR and/or Her3 and/or Her4, specifics as to the disease being treated, and dose regimen recommendations.

In each of these embodiments, the ligand can include an epidermal growth factor or a platelet-derived growth factor, and/or the tyrosine kinase receptor is EGFR, Her2, Her3, or Her4 complexes such that the aim of the method or composition is to inhibit the overexpression or activation of Her2 and/or growth factors, thereby inhibiting associated diseases such as cancer, angiogenesis associated with the growth of cancer or sarcoma, angiogenesis associated with cancer metastasis, angiogenesis associated with diabetic retinopathy, arteriosclerosis, restenosis, or psoriasis."

Other specific examples of "a disease caused by overexpression or activation of an erbB receptor, including Her2 and/or EGFR" include cancers such as brain tumor, pharyngeal cancer, laryngeal cancer, tongue cancer, esophageal cancer, gastric cancer, colorectal cancer, non-small cell lung cancer, pancreatic cancer, bile duct cancer, gallbladder cancer, liver cancer, renal cancer, bladder cancer, prostate cancer, breast cancer, ovarian cancer, cervical cancer, endometrial cancer, skin cancer, childhood solid cancer, bone tumor, hemangioma and the like, angiogenesis associated with diabetic retinopathy, arteriosclerosis, psoriasis and the like. Preferred are brain tumor, pharyngeal cancer, laryngeal cancer, tongue cancer, esophageal cancer, gastric cancer, colorectal cancer, non-small cell lung cancer, pancreatic cancer, bile duct cancer, gallbladder cancer, liver cancer, renal cancer, bladder cancer, prostate cancer, breast cancer, ovarian cancer, cervical cancer, endometrial cancer, skin cancer and the like and more preferred are brain tumor, gastric cancer, colorectal cancer, non-small cell lung cancer, pancreatic cancer, renal cancer, prostate cancer, breast cancer, ovarian cancer and the like.

In separate embodiments, the patient being treated or to whom the pharmaceutical composition is to be applied is a human.

This invention can be applied to treat cell proliferative disorders, such as cancers characterized by the over-activity or inappropriate activity of erbB receptors, when used alone or in combination with chemotherapy (e.g., cytotoxic chemotherapy or radiation or both) to halt resistance to currently available drugs. The invention may also be applied in combination with administering a pharmaceutically effective amount of an anti-cancer agent or performing a non-drug therapy or both on the patient, where the embodied compounds are administered at the same or different times as other anti-cancer agents, and/or where the non-drug therapy is surgery, hypertensive chemotherapy, genetherapy, thermotherapy, cryotherapy, photodynamic therapy, laser cauterization and/or radiotherapy.

The invention provides a novel class of Her2 and EGFR inhibitors that might halt the resistance to current tyrosine kinase inhibitors hence increase treatment efficacy, and as such provide an alternative to the use of current tyrosine kinase inhibitors. The discovered molecules, which are attainable for oral administration, can be used alone or in combination with cytotoxic drugs, hormonal agent, radiation, or other Her2 inhibitors to treat breast, lung, prostate, and other Her2-associated cancers. In addition, the discovered compounds exhibit great specificity against Her2/EGFR activity by selectively binding to only Her2 or Her2 associated dimers (for example Her2 homodimer, Her2-EGFR heterodimer, Her2-Her3 heterodimer and her2-her4 heterodimer). This might cause less severe side effects in comparison to the conventional tyrosine kinase inhibitors.

The small molecules describe by this invention can also be "tagged" with radio-isotopes for molecular imaging of tumor marker Her2 in vivo. Radio-labeled compounds are required for Positron Emission Tomography (PET) and Single Photon Emission Computed Tomography (SPECT). In vivo monitoring of the Her-2 expressing tumor is useful in monitoring the disease progression and assessing the treatment efficacy. Accordingly, the invention discloses a method of imaging an Her-2 expressing tumor comprising administering a marker to a patient having said Her-2 expressing tumor, said marker comprising a compound of Formula (I) containing an imaging enhancing agent.

In the present disclosure the singular forms "a," "an," and "the" include the plural reference, and reference to a particular numerical value includes at least that particular value, unless the context clearly indicates otherwise. Thus, for example, a reference to "a compound" is a reference to at least one of such compounds and equivalents thereof known to those skilled in the art, and so forth.

When values are expressed as approximations, by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. Where present, all ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

Generally terms are to be given their plain and ordinary meaning such as understood by those skilled in the art, in the context in which they arise. To avoid any ambiguity, however, several terms are described herein.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references that are provided throughout this document. The nomenclature used herein and the laboratory procedures in analytical chemistry, and organic synthetic chemistry described below are those well known and commonly employed in the art. Standard techniques, or modifications thereof, are used for chemical syntheses and chemical analyses.

Whenever a group of this invention is described as being "optionally substituted" that group may be unsubstituted or substituted with one or more of the substituents described for that group. Likewise, when a group is described as being "unsubstituted or substituted," if substituted, the substituent may be selected from the same group of substituents. Unless otherwise indicated, when a substituent is deemed to be "optionally substituted," or "substituted" it is meant that the substituent is a group that may be substituted with one or more group(s) individually and independently selected.

Each of the following terms (e.g., "alkyl," "heteroalkyl," "acyl," "alkoxy," "aryl," and "heteroaryl") include both substituted and unsubstituted forms of the indicated group, unless indicated otherwise.

The term "alkyl," by itself or as part of another substituent, means, unless otherwise stated, a straight or branched chain, or cyclic hydrocarbon group (cycloalkyl), or combination thereof, which may be fully saturated, mono- or polyunsaturated and can include di- and multivalent radicals, and can have a number of carbon atoms optionally designated (e.g., $C_{1-3}$ means one to three carbons). Examples of saturated hydrocarbon groups include, but are not limited to, groups such as methyl, ethyl, n-propyl, isopropyl.

An alkyl group of this invention may be substituted or unsubstituted. When substituted, the substituent group(s) may be one or more group(s) independently selected from cycloalkyl, aryl, heteroaryl, heteroalicyclyl, hydroxy, alkoxy, aryloxy, mercapto, alkylthio, arylthio, cyano, halo, oxo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, amino or substituted amino, protected hydroxyl, protected amino, protected carboxy and protected amido groups.

As used herein, "acyl" refers to an "RC(═O)—." An acyl group may contain an alkyl or aryl moiety, in which case it may be referred to as a carboxyalkyl or carboxyaryl group, respectively. Examples of acyl groups include, without limitation, formyl, acetyl, propionyl, butyryl, pentanoyl, pivaloyl, hexanoyl, heptanoyl, octanoyl, nonanoyl, decanoyl, undecanoyl, dodecanoyl and benzoyl. Presently preferred acyl groups are acetyl and benzoyl.

An acyl group of this invention may be unsubstituted or substituted. When substituted, the substituent(s) may be selected from the same groups disclosed above with regard to alkyl group substitution.

The term "alkoxy" is used in its conventional sense, and refers to those alkyl groups attached to the remainder of the molecule via an oxygen atom. Alkoxy groups include, but are not limited to methoxy, ethoxy, propoxy, trifluoromethoxy and difluoromethoxy.

An "amide" is a chemical moiety with formula —(R)$_n$—C(O)NHR' or —(R)$_n$—NHC(O)R', where n is the number of alkylene carbons from 0-1, R and R' are independently selected from the group consisting of alkyl, cycloalkyl, aryl, heteroaryl (bonded through a ring carbon) and heteroalicyclic (bonded through a ring carbon). An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end is known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

As used herein, an "ether" refers to an "—C—O—C—" group wherein either or both carbons may independently be part of an alkyl, alkenyl, alkynyl, aryl, heteroaryl or heteroalicyclyl group. A "halogenated ether" refers to an ether in which the groups to either side of the oxygen are both alkyl substituted with halogen.

The terms "halo" or "halogen," by themselves or as part of another substituent, mean, unless otherwise stated, a fluorine, chlorine, bromine, or iodine atom. Preferred halogens are chloro, iodo, and fluoro.

The term "heteroalkyl," by itself or in combination with another term, means, unless otherwise stated, a stable straight or branched chain, or cyclic hydrocarbon group, or combinations thereof, consisting of a number of carbon atoms and at least one heteroatom selected from the group consisting of O, N, Si and S, and wherein the nitrogen, carbon and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), carbon-11 ($^{11}$C), carbon-14 ($^{14}$C), nitrogen-13 ($^{13}$N), sulfur-35 ($^{35}$S), iodine-131 ($^{131}$I), or fluorine-18 ($^{18}$F). When indicated as such, radiolabled molecules contain isotopes enriched above their natural abundances. Such radioisotopes can be prepared either by synthetic means using commercially available precursors and reactants generally recognized as providing by substitution the particular element of interest (e.g., halide substitution using radioactive halides) or by cyclotron irradiation of the pre-formed molecules. All isotopic variations of the compounds of the present invention, whether radioactive or not, are intended to be encompassed within the scope of the present invention.

As used herein, "phenyl" refers to a 6-member aryl group. A phenyl group may be unsubstituted or substituted. When substituted the substituent(s) is/are one or more, preferably one or two, group(s) independently selected from the group consisting of halogen, hydroxy, protected hydroxy, cyano, nitro, alkyl, alkoxy, acyl, acyloxy, carboxy, protected carboxy, carboxymethyl, protected carboxymethyl, hydroxymethyl, protected hydroxymethyl, amino or substituted amino, carboxamide, protected carboxamide, N-alkylcarboxamide, protected N-alkylcarboxamide, N,N-dialkylcarboxamide, trifluoromethyl, N-alkylsulfonylamino, N-(phenylsulfonyl) amino and phenyl (resulting in the formation of a biphenyl group).

As used herein, "amino protecting group" refers to a group commonly employed to keep (i.e., to "block" or "protect") an amino group from reacting with a reagent while it reacts with an intended target functional group of a molecule.

Examples of amino protecting groups include, without limitation, formyl ("For"), trityl, phthalimido, trichloroacetyl, chloroacetyl, bromoacetyl, iodoacetyl groups, t-butoxycarbonyl ("Boc"), 2-(4-biphenylyl)propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluoyl)propyl-2-oxycarbonyl, cyclopentanyloxycarbonyl, 1-methylcyclopentanyloxycarbonyl, cyclohexanyloxy-carbonyl, 1-methylcyclohexanyloxycarbonyl, 2-methylcyclohexanyloxycarbonyl, 2-(4-toluoylsulfonyl)-ethoxycarbonyl, 2-(methylsulfonyl)ethoxycarbonyl, 2-(triphenylphosphino)-ethoxycarbonyl, 9-fluorenylmethoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyl-oxycarbonyl, 2,2,2-trichloroethoxycarbonyl, 2-ethynyl-2-propoxycarbonyl, cyclopropyl-methoxycarbonyl, isobornyloxycarbonyl, 1-piperidyloxycarbonyl, benzyloxycarbonyl ("Cbz"), 4-phenylbenzyloxycarbonyl, 2-methylbenzyloxy-carbonyl, -2,4,5-tetramethylbenzyloxycarbonyl ("Tmz"), 4-methoxybenzyloxy-carbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyl-oxycarbonyl, 4-bromobenzyloxycarbonyl, 3-bromobenzyloxycarbonyl, 4-nitrobenzyloxy-carbonyl, 4-cyanobenzyloxycarbonyl, 4-(decyloxy)benzyloxycarbonyl, benzoylmethylsulfonyl, dithiasuccinoyl ("Dts"), 2-(nitro)phenylsulfenyl ("Nps"), and diphenyl-phosphine oxide. The species of amino-protecting group employed is not critical so long as the derivatized amino group is stable to the conditions of the subsequent reaction(s) and can be removed at the appropriate point without disrupting the remainder of the molecule. Presently preferred amino-protecting groups are Boc, Cbz and Fmoc.

Descriptions of these and other amino-protecting groups may be found in T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984.

As used herein, the term "carboxy protecting group" refers to a labile ester commonly used to block or protect a carboxylic acid while reactions are carried out on other functional groups on the compound. Examples of carboxy protecting groups include, without limitation, t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4''-trimethoxytrityl, 2-phenylpropyl, trimethylsilyl, t-butyldimethylsilyl, phenacyl, 2,2,2-trichloroethyl, -(trimethylsilyl)ethyl, -(di(n-butyl)methylsilyl) ethyl, p-toluenesulfonylethyl, 4-nitrobenzylsulfonylethyl, allyl, cinnamyl, and 1-(trimethylsilylmethyl)-propenyl. The ester employed is not critical so long as it is stable to the conditions of subsequent reaction(s) and can be removed at the appropriate point without disrupting the remainder of the molecule. Further examples of carboxy-protecting groups are found in E. Haslam, "*Protective Groups in Organic Chemistry*," J. G. W. McOmie, Ed., Plenum Press, New York, N.Y., 1973, Chapter 5, and T. W. Greene and P. G. M. Wuts, "*Protective Groups in Organic Synthesis*," 2nd ed., John Wiley and Sons, New York, N.Y., 1991, Chapter 5.

As used herein, a "hydroxyl protecting group" refers to a readily cleavable group that replaces the hydrogen of the hydroxyl group, such as, without limitation, tetrahydropyranyl, 2-methoxypropyl, 1-ethoxyethyl, methoxymethyl, 2-methoxyethoxymethyl, methylthiomethyl, t-butyl, t-amyl, trityl, 4-methoxytrityl, 4,4'-dimethoxytrityl, 4,4',4''-trimethoxytrityl, benzyl, allyl, trimethylsilyl, (t-butyl)dimethylsilyl, and 2,2,2-trichloroethoxycarbonyl. The species of hydroxyl protecting groups is not critical so long as the derivatized hydroxyl group is stable to the conditions of subsequent reaction(s) and can be removed at the appropriate point without disrupting the remainder of the molecule. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3.

By "perhaloalkyl" it is meant an alkyl moiety where all of the hydrogen atoms normally present on the alkyl are replaced by a halogen. Thus, for example, a perchloroalkyl is an alkyl moiety where all of the carbon atoms not connected to the rest of the molecule are connected to chlorine atoms.

Throughout the present disclosure, when a particular compound comprises a chiral center, the scope of the present disclosure also includes compositions comprising the racemic mixture of the two enantiomers, as well as compositions comprising each enantiomer individually substantially free of the other enantiomer. Thus, for example, contemplated herein is a composition comprising the S enantiomer substantially free of the R enantiomer, or a composition comprising the R enantiomer substantially free of the S enantiomer. By "substantially free" it is meant that the composition comprises less than 10%, or less than 8%, or less than 5%, or less than 3%, or less than 1% of the minor enantiomer. If the particular compound comprises more than one chiral center, the scope of the present disclosure also includes compositions comprising a mixture of the various diastereomers, as well as compositions comprising each diastereomer substantially free of the other diastereomers. The recitation of a compound, without reference to any of its particular diastereomers, includes compositions comprising all four diastereomers, compositions comprising the racemic mixture of R,R and S,S isomers, compositions comprising the racemic mixture of R,S and S,R isomers, compositions comprising the R,R enantiomer substantially free of the other diastereomers, compositions comprising the S,S enantiomer substantially free of the other diastereomers, compositions comprising the R,S enantiomer substantially free of the other diastereomers, and compositions comprising the S,R enantiomer substantially free of the other diastereomers.

Inhibiting Cell Proliferative Disorders

The term "therapeutic agent" is intended to mean a compound that, when present in a therapeutically effective amount, produces a desired therapeutic effect on a patient. For example, an "effective amount" of a compound for inhibiting Her2/neu action is an amount of a compound or composition that is sufficient to inhibit, reduce, or otherwise mitigate an undesirable effect of Her2/neu action. Such inhibition may occur for example, and without limitation, via a direct interaction, and/or through a competitive interaction, or via an allosteric interaction with a corresponding receptor.

Medical Imaging

These small molecules can also be conjugated, or "tagged" with fluorescent probes or radio-isotopes for molecular imaging of tumor marker Her2 in vivo. Long wavelength fluorescent probes are suitable for optical imaging, while radio labeled compounds are required for Positron Emission Tomography (PET) and Single Photon Emission Computed Tomography (SPECT).

Positron Emission Tomography (PET) is a precise and sophisticated, non-invasive technique using isotopes produced in a cyclotron. A positron-emitting radionuclide is introduced, usually by injection, and accumulates in the target tissue. As it decays it emits a positron, which promptly combines with a nearby electron resulting in the simultaneous emission of two identifiable gamma rays in opposite directions. These are detected by a PET camera and give very precise indication of their origin.

Salts and Derivatives

The term "pharmaceutically acceptable salt" means those salts of compounds of the invention that are safe and effective for use in a subject and that possess the desired biological activity. Pharmaceutically acceptable salts include salts of acidic or basic groups present in compounds of the invention. Various pharmaceutically acceptable salts, ether derivatives, ester derivatives, acid derivatives, and aqueous solubility altering derivatives of the active compound also are encompassed by the present invention. The present invention further includes all individual enantiomers, diastereomers, racemates, and other isomers of the compound. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

As the compounds of the invention may contain charged side chains or termini, they may be included in any of the above-described formulations as the free acids or bases or as pharmaceutically acceptable salts. Pharmaceutically acceptable salts are those salts which substantially retain the physiological activity of the free bases and which are prepared by reaction with inorganic acids. Pharmaceutical salts tend to be more soluble in aqueous and other protic solvents than are the corresponding free base forms.

Suitable salts of the compound include, but are not limited to, acid addition salts, such as those made with hydrochloric, hydrobromic, hydroiodic, hydrofluoric, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as lithium, sodium, and potassium salts; alkaline earth metal salts, such as calcium and magnesium salts; salts formed from Lewis acids, such as boron trifluoride; and salts formed with organic or inorganic ligands, such as quaternary ammonium salts (for example, tris(hydroxymethyl)aminomethane salts).

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound of the present invention. For a review on pharmaceutically acceptable salts see Berge et al., 66 J. Pharm. Sci 1-19 (1977), incorporated herein by reference.

Prodrugs and active metabolites of compounds disclosed herein are also within the scope of the invention.

A prodrug is a pharmacologically inactive compound that is converted into a pharmacologically active agent by a metabolic transformation or any other chemical or biological process (e.g., hydrolysis). For example, in vivo, a prodrug can be acted on by naturally occurring enzyme(s) resulting in liberation of the pharmacologically active agent. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in "Design of Prodrugs," ed. H. Bundgaard, Elsevier, 1985.

An active metabolite is a compound that results from metabolism of another compound after administration of the latter to a subject. Metabolites can be identified by techniques well-known in the art.

Formulation and Administration

The compounds of the invention will generally be used in an amount effective to achieve the intended purpose. For use to treat, inhibit, or prevent Her2-mediated cell proliferative disorders, the compounds of the invention, or pharmaceutical compositions thereof, are administered or applied in a therapeutically effective amount. By "therapeutically effective amount" is meant an amount effective ameliorate or prevent the symptoms, prolong the survival of, or otherwise mitigate the undesirable effects of the disease for which the patient is being treated. Determination of a therapeutically effective amount is well within the capabilities of those skilled in the art, especially in light of the detailed disclosure provided herein. The term "prevent" as used herein to describe the action of inhibiting cell proliferation or the growth of tumors, or ameliorating the symptoms, prolonging the survival of, or otherwise mitigating the undesirable effects of the disease for which the patient is being treated.

For detection of expression or activity of Her2 and/or EGFR, a tissue (cancer tissue, blood vessel wall tissue, skin, oral mucosa etc.) or a body fluid (blood, lymph) and the like, which is obtained from patients, is applied to a test to detect expression or activity of Her2 and/or EGFR. Such tests are known to those skilled in the art. With regard to the treatment of some conditions, for example, atherosclerosis, certain people may be identified as being at high risk, for example, due to genetic, environmental or historical factors. Compounds within the scope of the present invention can be used in preventing or delaying the occurrence or reoccurrence of such conditions or otherwise treating the condition.

As mentioned above, the inhibitor of the present invention is an effective treatment method of cancer patients and also expected to be an agent for the prophylaxis and/or treatment of preventing transition from hormone sensitive cancer to resistant cancer in prostate cancer and breast cancer. Moreover, it is expected to an agent for the prophylaxis and/or treatment of angiogenesis associated with the growth of solid cancer and sarcoma, angiogenesis associated with cancer metastasis, angiogenesis associated with diabetic retinopathy, arteriosclerosis, psoriasis and the like.

The "overexpression or activation of Her2 and/or EGFR" is an expression or activity not less than the expression amount or activity necessary for homeostasis of living organisms, and the expression or activity not less than the expression amount or activity necessary for normal tissue of the same origin.

The "patients showing overexpression or activation of Her2 and/or EGFR" means the patients wherein at least one of Her2 and EGFR is excessively expressed or activated, and preferably the patients wherein both are excessively expressed or activated. The Her2 and/or EGFR inhibitor of the present invention is characterized by administration for the treatment of patients, wherein Her2 and/or EGFR are/is excessively expressed or activated as mentioned above.

The "Her2 and/or EGFR inhibitor" of the present invention is preferably a Her2 and EGFR inhibitor to be administered to patients wherein Her2 and EGFR are excessively expressed or activated, and may be a mixture of a Her2 inhibitor and an EGFR inhibitor. It is possible to use a Her2 inhibitor and an EGFR inhibitor simultaneously, separately or at time intervals. In other words, it is possible to administer a Her2 inhibitor and an EGFR inhibitor simultaneously, separately or, for example, in a staggered manner in a single day or at given time intervals for several days to several weeks or several months, by various different routes.

The amount of compound administered will, of course, be dependent on the subject being treated, on the subject's weight, the severity of the affliction, the manner of administration and the judgment of the prescribing physician. However, to the extent that these compounds provide improved activity relative to other known small molecules in in vivo, in vitro, and animal studies, in the broadest sense, recommended dosages are those similar to those currently prescribed for other small molecules for this same purpose.

The therapy may be repeated intermittently while symptoms detectable or even when they are not detectable. The therapy may be provided alone or in combination with other drugs.

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use human. The dosage of the compounds described lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, p. 1). Preferred dosages range from 1 nM to 500 mM.

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterille administration, and other dosage forms for systemic delivery of active ingredients. In a preferred embodiment, the dosage form is suitable for oral administration.

To prepare such pharmaceutical dosage forms, one or more of the aforementioned compounds or a pharmaceutically acceptable salt thereof, are intimately admixed with a pharmaceutical carrier according to conventional pharmaceutical compounding techniques. The carrier may take a wide variety of forms depending on the form of preparation desired for administration.

The compounds of the invention, may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active peptides or peptide analogues into preparations which can be used pharmaceutically. Proper formulation is dependent upon the route of administration chosen.

For parenteral formulations, the carrier will usually comprise sterile water, though other ingredients, for example, ingredients that aid solubility or for preservation, may be included. Injectable solutions may also be prepared in which case appropriate stabilizing agents may be employed.

Parenteral administration may comprise any suitable form of systemic delivery or delivery directly to the CNS. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

In preparing the compositions in oral dosage form, any of the usual pharmaceutical media may be employed. Thus, the compounds can be readily formulated by combining the compounds, salts, or analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

In some applications, it may be advantageous to utilize the active agent in a "vectorized" form, such as by encapsulation of the active agent in a liposome, micelle, or other encapsulant medium, or by fixation of the active agent, e.g., by covalent bonding, chelation, assembly, or associative coordination, on a suitable biomolecule, such as those selected from proteins, lipoproteins, glycoproteins, and polysaccharides.

For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For solid oral preparations such as, for example, powders, capsules, caplets, and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

Treatment methods of the present invention using formulations suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

For buccal administration, the compounds may take the form of tablets, lozenges, etc. formulated in conventional manner.

For topical administration the compounds of the invention may be formulated as solutions, gels, ointments, creams, suspensions, etc. as are well-known in the art.

Formulations suitable for parenteral administration usually comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Systemic formulations include those designed for administration by injection, e.g. subcutaneous, intravenous, intramuscular, intrathecal or intraperitoneal injection, as well as those designed for transdermal, transmucosal, oral or pulmonary administration.

Nasal and other mucosal spray formulations (e.g., inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

For administration by inhalation, the compounds for use according to the present invention are conveniently delivered in the form of an aerosol spray from pressurized packs or a nebulizer, with the use of a propellant acceptable as suitable by the pharmaceutical industry. Suitable propellants include, but are not limited to dichlorodifluoromethane, trichlorofluoromethane, dichlorotetrafluoroethane, 1,1,1,2-tetrafluoroethane, P-227ea, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For injection, the compounds of the invention may be formulated in aqueous solutions, preferably in physiologically compatible buffers such as Hank's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

The compounds may also be formulated in rectal or vaginal compositions such as suppositories or retention enemas, e.g., containing conventional suppository bases such as cocoa butter or other glycerides, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippingcott Williams and Wilkins: Philadelphia, Pa., 2000.

The formulation of the present invention can have immediate release, sustained release, delayed-onset release or any other release profile known to one skilled in the art.

The subject receiving the pharmaceutical composition is preferably an animal, including, but not limited to, an animal such a cow, horse, sheep, pig, chicken, turkey, quail, cat, dog, mouse, rat, rabbit, and guinea pig, and is more preferably a mammal, and most preferably a human.

The amount of the active agent to be administered can typically range from between about 0.01 to about 25 mg/kg/day, preferably from between about 0.1 to about 10 mg/kg/day and most preferably from between about 0.2 to about 5 mg/kg/day. It will be understood that the pharmaceutical formulations of the present invention need not necessarily contain the entire amount of the agent that is effective in treating the disorder, as such effective amounts can be reached by administration of a plurality of doses of such pharmaceutical formulations.

In a preferred embodiment of the present invention, the compounds are formulated in capsules or tablets, preferably containing 25 to 200 mg of the compounds of the invention, and are preferably administered to a patient at a total daily dose of about 0.5 mg to about 2 g, preferably about 7.5 mg to about 750 mg, more preferably about 15 mg to 750 mg, and most preferably from about 50 to about 200 mg.

A pharmaceutical composition for parenteral administration contains from about 0.01% to about 100% by weight of the active agents of the present invention, based upon 100% weight of total pharmaceutical composition.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day. Some preferred dosages range from 1 nM to 500 mM. Some preferred dosages range from 1 mM to 500 mM. Some preferred dosages range from 1 mg to 500 mg. Some preferred dosages range from 1000 mg to 3000 mg. Some preferred dosages range from 1500 mg to 2500 mg.

In cases of local administration or selective uptake, the effective local concentration of the compounds may not be related to plasma concentration. One having skill in the art will be able to optimize therapeutically effective local dosages without undue experimentation.

EXPERIMENTAL

Example 1

Screening Studies

Targeted molecules were screened in vitro for anti-tumor activity using a modified anchorage-dependent growth of transformed cell assay, as described in Fukazawa et al. (1995), Anal. Biochem., 10:83-90. Anchorage-independent growth capability is perhaps the best indicator of the malignant phenotype and is determined by efficiency of cells to form colonies in soft agar (Drebin, et al., *Cell* 41, 697-706 (1985)). All experiments were conducted in 6 cm dishes in triplicate. Agar bottom layers consisted of 3 ml 0.25% agarose/DMEM (Dulbecco's Modified Eagle Medium) supplemented with 10% FBS (Fetal Bovine Serum), 2 mM L-glutamine, and 100 u/ml Penicillin/1 µg/ml Streptomycin. About 1000-2000 cells T6-17/SK-BR-3 are layered on the top in 1 ml 0.18% agarose/DMEM, 10% FBS, 2 mM L-glutamine, and 100 µ/ml Penicillin/1 µg/ml Streptomycin. Cultures were treated every 3 days with 0.5 ml of supplemented DMEM containing measured amounts of the Her2 inhibitors, or DMSO (dimethyl sulfoxide) alone. On the day before the colonies were counted, the samples were incubated with 1 ml of Hank's Balanced Salt Solution containing 1 mg/ml p-iodonitrotetrazolium violet (INT, Sigma) to stain colonies. The next day, colonies were counted using a 7× achromatic magnifying eyepiece (Bausch and Lomb). Triplicate cultures were counted on day 21 and will be verified by at least two different persons. Bars represent the mean values±one standard deviation.

Figure 2:
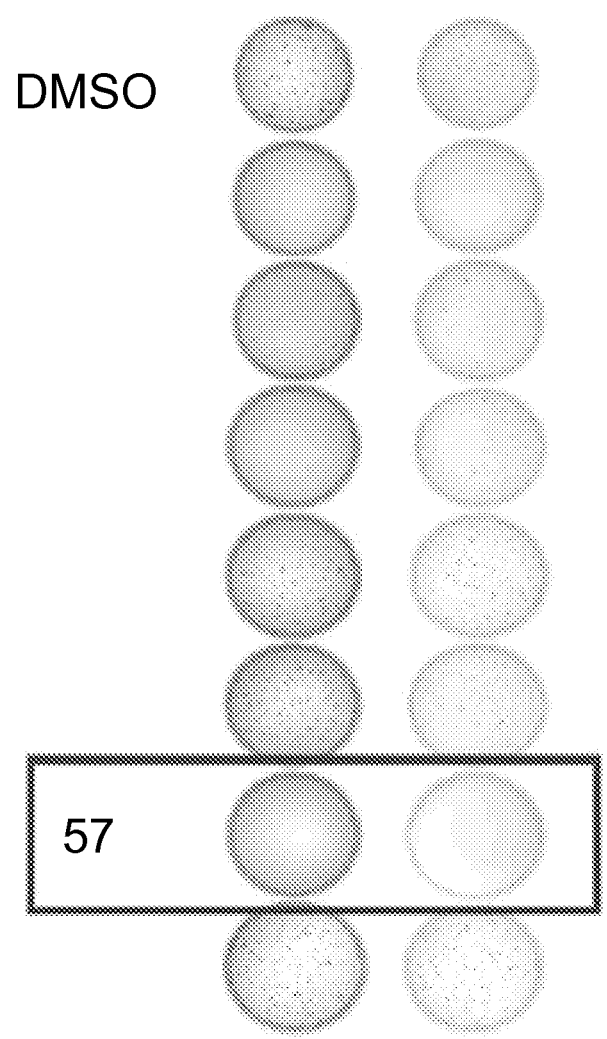
FIG. 2 shows representative illustrations of plates as developed from Example 1. Again, plates for compound #S22_57 are highlighted (as "057"), showing reduced cellular growth in culture relative to DMSO control.

The results of this testing is shown in FIG. 1. FIG. 2 shows representative plates for the individual compounds.

Example 2

Inhibition of Proliferation of Several Cell Lines

Figure 3:
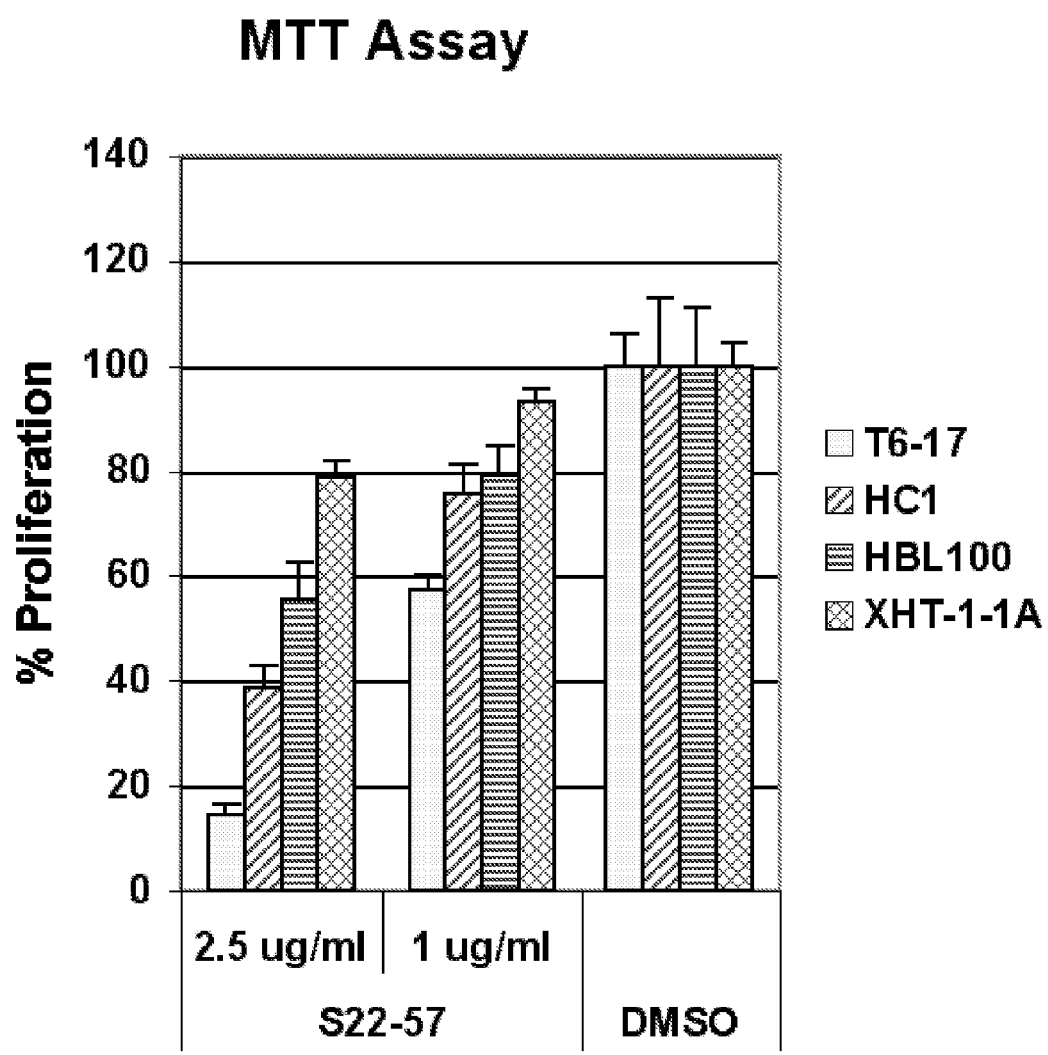
FIG. 3 shows the inhibition of cell proliferation by HER2/neu inhibitors, as described in Example 2.

The activity of S22-57 in cell proliferation assays using different cell lines was examined. T6-17 is a murine cell line engineered to express human HER2/neu. HC1 is a human non-small lung cancer cell line with upregulated HER2/neu and resistant to anti-EGFR antibody cetuximab. HBL100 is an immortalized human breast cancer cell line. XHT-1-1A are mouse NIH3T3 cells transformed by Harvey-RAS (XHT-1-1a) previously developed and used (Drebin, et al., *Cell* 41, 697-706 (1985)). Both HBL100 and XHT-1-1A are used as controls. To measure cell proliferation, we used the modified 3-[4,5-dimethylthiazol-2-yl]-2,5-diphenyl tetrazolium bromide (MTT) assay as previously described (Masuda, et al., *Oncogene* 25, 7740-7746 (2006)). Cells (2000-5000 cells/well) were seeded in 96-well plates in the presence of inhibitors with different concentration and incubated at 37° C. in a humidified 5% CO2 atmosphere. After 72 h, cells were incubated in fresh medium for another 4 hours before a total of 25 µl of MTT solution (5 mg/ml in PBS) was added to each well, and after 2 h of incubation at 37° C., 100 µl of the extraction buffer (20% w/v SDS, 50% N,N-dimethyl formamide, pH 4.7) was added. After an overnight incubation at 37° C., the optical density at 570 nm was measured using a Tecan ELISA reader. FIG. 3 shows the results of experiments in which cells were treated with inhibitors at indicated doses for three days. Proliferation of cells was measured by the MTT assay. As shown in FIG. 3, S22-05 at 10 µg/ml selectively inhibited the proliferation of T6-17 and HC1 cells. S22-57 also inhibited T6-17 and HC1 dose-dependently.

Example 3

Inhibition of HER2 Phosphorylation in HC1 Cells

Figure 4:
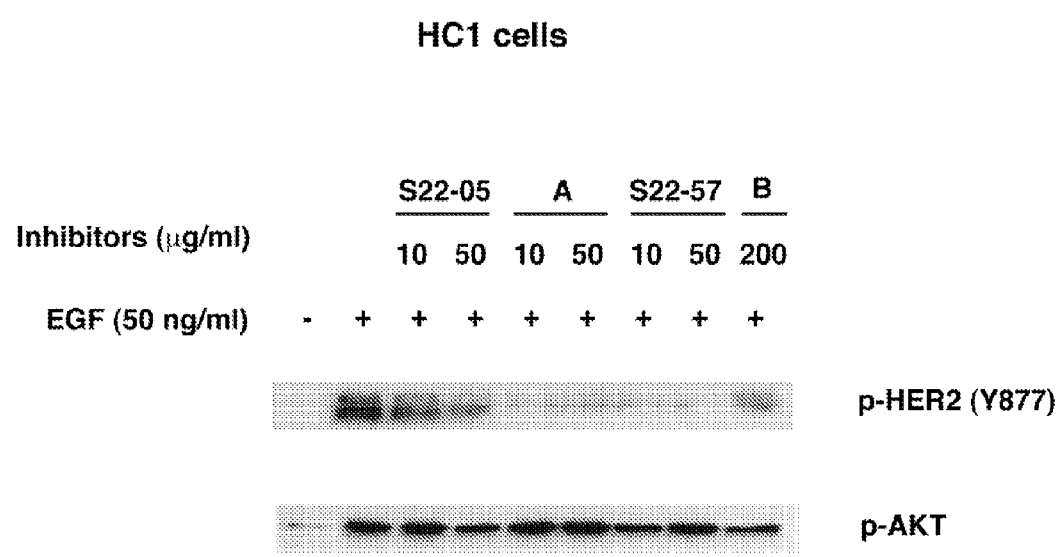
FIG. 4. shows the inhibition of HER2 phosphorylation in HC1 cells, as described in Example 3.

The effect of S22-57 was also examined in the cetuximab-resistant non-small cell lung cancer cell line HC1. Confluent HC1 cells were first serum starved for 24 hours before exposed to inhibitors as indicated for 1 hour. Cells were then stimulated by EGF (50 ng/ml) for 10 minutes. Cell lysates were collected for western blot using antibodies to HER2Y877 or p-AKT, following protocols suggested by manufacturers. Both antibodies were purchased from Cell Signaling. As shown in FIG. 4, S22-57 inhibited EGF-stimulated phosphorylation of HER2 at Y877.

What is claimed:

1. A method of inhibiting a cell proliferative disorder characterized by over-activity and/or inappropriate activity of Her2, the method comprising administering to a patient in need of such treatment a pharmaceutically effective amount of a compound of Formula (I), or a pharmaceutically acceptable salt or prodrug thereof:

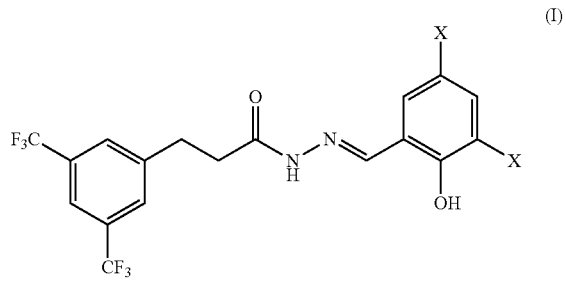

(I)

wherein X is independently at each occurrence alkyl, halo, perfluoromethyl, hydroxy, carboxylic acid, ester, amide, substituted alkoxy, substituted thiol, substituted acyl, nitrile, or substituted amino group.

2. The method of claim 1 wherein X is halo.

3. The method of claim 1 wherein the compound of Formula (I) is

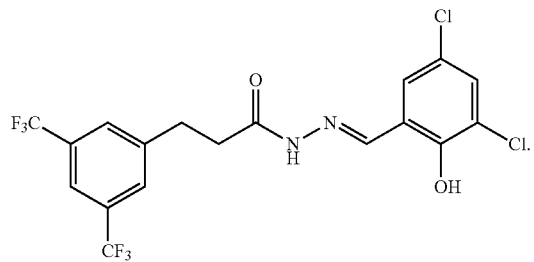

4. The method of claim 1 wherein the cell proliferative disorder is cancer.

5. The method of claim 1 wherein the cell proliferative disorder affects a breast, prostate, lung, pancreas, ovary, or stomach.

6. The method of claim 1 wherein the patient is a human.

7. The method of claim 1 further comprising administering a pharmaceutically effective amount of an anti-cancer agent or performing a non-drug therapy or both to the patient.

8. The method of claim 7 wherein the compound of Formula (I) and the anti-cancer agent are administered at the same time.

9. The method of claim 7 wherein the non-drug therapy is surgery, hypertensive chemotherapy, genetherapy, thermotherapy, cryotherapy, photodynamic therapy, laser cauterization and/or radiotherapy.

10. A pharmaceutical composition comprising a compound of Formula (I), or a pharmaceutically acceptable salt or prodrug thereof, in an amount effective to inhibit a cell proliferative disorder characterized by over-activity and/or inappropriate activity of Her2, and a pharmaceutically acceptable excipient:

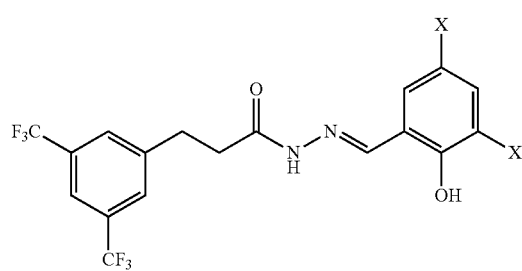

(I)

wherein X is independently at each occurrence an alkyl, halo, perfluoromethyl, hydroxy, carboxylic acid, ester, amide, substituted alkoxy, substituted thiol, substituted acyl, nitrile, or substituted amino group.

11. The composition of claim 10 wherein X is halo.

12. The composition of claim 10 wherein the compound of Formula (1) is

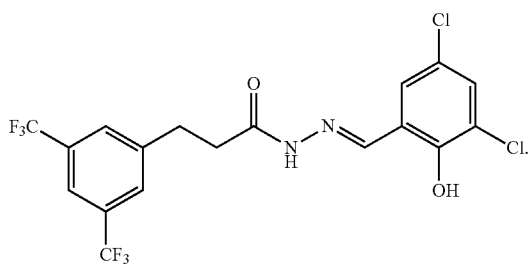 [SMILES: O=C(CCc1cc(C(F)(F)F)cc(C(F)(F)F)c1)N/N=C/c1cc(Cl)cc(Cl)c1O]

13. The composition of claim 10 wherein the cell proliferative disorder is cancer.

14. The composition of claim 10 wherein the cell proliferative disorder affects a breast, prostate, lung, pancreas, ovary, or stomach.

15. The composition of claim 10 wherein the cell proliferative disorder is psoriasis, atherosclerosis or restenosis.

16. The composition of claim 10 wherein the patient is a human.

17. A commercial package comprising the pharmaceutical composition of claim 10, at least one anti-cancer agent, and a written matter associated therewith, the written matter stating that the pharmaceutical composition can or should be used for treatment of a disease caused by overexpression or activation of Her2.

\* \* \* \* \*